(12) United States Patent
Den Boef et al.

(10) Patent No.: US 7,315,384 B2
(45) Date of Patent: Jan. 1, 2008

(54) INSPECTION APPARATUS AND METHOD OF INSPECTION

(75) Inventors: Arie Jeffrey Den Boef, Waalre (NL); Mircea Dusa, Campell, CA (US)

(73) Assignee: ASML Netherlands B.V., Veldhoven (NL)

( * ) Notice: Subject to any disclaimer, the term of this patent is extended or adjusted under 35 U.S.C. 154(b) by 159 days.

(21) Appl. No.: 11/125,322

(22) Filed: May 10, 2005

(65) Prior Publication Data

US 2006/0256324 A1    Nov. 16, 2006

(51) Int. Cl.
G01B 11/14 (2006.01)
(52) U.S. Cl. ...................... 356/625; 356/628
(58) Field of Classification Search ........ 356/625–640, 356/400, 499, 509, 445, 446, 601, 512–513, 356/453, 485, 492; 250/548
See application file for complete search history.

(56) References Cited

U.S. PATENT DOCUMENTS

| | | | |
|---|---|---|---|
| 5,703,692 A | 12/1997 | McNeil et al. | 356/445 |
| 5,880,838 A | 3/1999 | Marx et al. | 356/351 |
| 5,963,329 A | 10/1999 | Conrad et al. | 356/372 |
| 6,608,690 B2 | 8/2003 | Niu et al. | 356/635 |
| 6,699,624 B2 | 3/2004 | Niu et al. | 430/5 |
| 6,704,661 B1 | 3/2004 | Opsal et al. | 702/27 |
| 6,721,691 B2 | 4/2004 | Bao et al. | 702/189 |
| 6,738,138 B2 | 5/2004 | Wei | 356/369 |
| 6,753,961 B1 | 6/2004 | Norton et al. | 356/364 |
| 6,768,983 B1 | 7/2004 | Jakatdar et al. | 706/46 |
| 6,772,084 B2 | 8/2004 | Bischoff et al. | 702/127 |
| 6,785,638 B2 | 8/2004 | Niu et al. | 702/189 |
| 6,813,034 B2 | 11/2004 | Rosencwaig et al. | 356/601 |
| 6,819,426 B2 | 11/2004 | Sezginer et al. | 356/401 |
| 6,856,408 B2 | 2/2005 | Raymond | 356/601 |
| 6,919,964 B2 | 7/2005 | Chu | 356/601 |
| 6,928,628 B2 | 8/2005 | Seligson et al. | 716/4 |
| 6,972,852 B2 | 12/2005 | Opsal et al. | 356/625 |
| 6,974,962 B2 | 12/2005 | Brill et al. | 250/548 |
| 6,987,572 B2 | 1/2006 | Lakkapragada et al. | 356/601 |
| 7,046,376 B2 | 5/2006 | Sezginer | 356/601 |
| 7,061,615 B1 | 6/2006 | Lowe-Webb | 356/401 |
| 7,061,623 B2 | 6/2006 | Davidson | 356/497 |
| 7,061,627 B2 | 6/2006 | Opsal et al. | 356/601 |
| 7,068,363 B2 | 6/2006 | Bevis et al. | 356/237.5 |
| 2004/0109173 A1* | 6/2004 | Finarov et al. | 356/625 |
| 2004/0119970 A1 | 6/2004 | Dusa et al. | 356/237.1 |
| 2004/0212812 A1* | 10/2004 | Bischoff et al. | 356/601 |

(Continued)

OTHER PUBLICATIONS

Ausschnitt, Christopher P., A New Approach to Pattern Metrology, Proc. of SPIE, vol. 5375, pp. 51-65 (Feb. 2004).

*Primary Examiner*—Gregory J. Toatley, Jr.
*Assistant Examiner*—Tri Ton
(74) *Attorney, Agent, or Firm*—Pillsbury Winthrop Shaw Pittman LLP

(57) ABSTRACT

An inspection apparatus, comprising; an illumination system configured to provide an illumination beam for irradiating a target; a first detection system configured to detect radiation scattered from the target in a non-zero order diffraction direction; and the detection system comprises a dispersive element for dispersion of the radiation scattered from the target in the non-zero order diffraction direction and a radiation sensitive device constructed and arranged to measure the intensity of the radiation dispersed by the dispersive element.

19 Claims, 1 Drawing Sheet

U.S. PATENT DOCUMENTS

| | | | |
|---|---|---|---|
| 2005/0018189 A1* | 1/2005 | Hampton et al. | 356/369 |
| 2005/0078320 A1* | 4/2005 | Mueller et al. | 356/512 |
| 2006/0033921 A1 | 2/2006 | Den Boef et al. | 356/446 |
| 2006/0066855 A1 | 3/2006 | Den Boef et al. | 356/401 |
| 2006/0126074 A1 | 6/2006 | Van Der Werf et al. | 356/489 |
| 2006/0139592 A1 | 6/2006 | Den Boef et al. | 355/53 |

* cited by examiner

INSPECTION APPARATUS AND METHOD OF INSPECTION

BACKGROUND OF THE INVENTION

1. Field of the Invention

The present invention relates to an inspection apparatus and a method for the inspection of a target on a substrate, for example, a surface of a substrate being processed in the semiconductor industry.

2. Description of the Related Art

A lithographic projection apparatus is used to image a pattern (e.g., in a mask) onto a substrate that is at least partially covered by a layer of radiation-sensitive material (resist). Prior to this imaging, the substrate may undergo various procedures, such as priming, resist coating and a soft bake. After exposure, the substrate may be subjected to other procedures, such as a post-exposure bake (PEB), development, and a hard bake. These procedures are used as a basis to pattern an individual layer of a device, e.g., an IC. Such a patterned layer may then undergo various processes such as etching, ion-implantation (doping), metallization, oxidation, chemo-mechanical polishing, etc., all intended to finish off an individual layer. If several layers are required, then the whole procedure, or a variant thereof, will have to be repeated for each new layer. Eventually, an array of devices will be present on the substrate (wafer). These devices are then separated from one another by a technique such as dicing or sawing, whence the individual devices can be mounted on a carrier, connected to pins, etc. Each procedure or process may be followed by an inspection of the substrate in an inspection apparatus. With the inspection results, one may optimize or improve the procedures prior to the inspection or if a large part of the substrate is faulty, the patterned layer may be stripped off the substrate and the stripped patterned layer may be reapplied through exposure and/or other lithographic processing. Further information regarding lithographic processes used in, for example, the semiconductor industry can be obtained, for example, from the book "Microchip Fabrication: A Practical Guide to Semiconductor Processing," Third Edition, by Peter van Zant, McGraw Hill Publishing Co., 1997, ISBN 0-07-067250-4, incorporated herein by reference.

The inspection apparatus may be used for surface inspection in semiconductor processing and may measure properties like line width, pitch, and critical dimension (CD) of the patterned layer. The apparatus may also measure the relative placement of one layer to another layer (i.e., overlay) and the layer thickness of a resist layer. An example of such an inspection apparatus, named MOXIE is described in "A new approach to Pattern Metrology" by Cristopher P. Ausschnitt, proceedings of SPIE, Vol. 5375, page 51 to 65, incorporated herein by reference.

The MOXIE sensor detects at least one non-zero diffracted order from a grating target in a "diffraction" channel and the reflected energy from both patterned and un-patterned illuminated areas in a "reflection" channel. The sensor is configured such that the illumination in the 300-700 nm range is directed along the direction of the grating period of the target at an angle relative to the Z-axis (the Z-axis being perpendicular to the target). The non-zero diffraction order rays are directed substantially in the Z-direction and a cylindrical lens in the "diffraction" channel projects the first order diffracted rays onto a detector array in a direction along the direction of the grating period. The detector array will measure the intensity of the non-zero diffraction order as a function of the wavelength.

SUMMARY OF THE INVENTION

Accordingly, it would be useful to provide an improved inspection apparatus.

According to an aspect of the invention, there is provided an inspection apparatus including an illumination system configured to provide an illumination beam for irradiating a target, a first detection system configured to detect radiation diffracted from the target in a non-zero order diffraction direction, and wherein the detection system includes a first dispersive element for dispersion of the radiation diffracted from the target in the non-zero order diffraction direction and a first radiation sensitive device constructed and arranged to measure the intensity of the radiation dispersed by the first dispersive element.

Another aspect of embodiments of the invention is that the illumination beam has a broad bandwidth (e.g., in the range of 300 to 700 nm) and the detector is constructed and arranged to measure the intensity of the radiation diffracted from the target as a function of the wavelength. The illumination beam may be, for example, irradiated from a xenon source.

The first dispersive element may be lateral dispersive element (e.g., a prism or a grating) dispersing the radiation in a lateral first direction and the radiation sensitive device may be divided in said first direction in parts, each part constructed and arranged to measure the intensity of the radiation received on that part.

A further aspect of embodiments of the invention includes a lens for projecting the target upon the first radiation sensitive device which may be a CCD array.

The inspection apparatus may further include a second detection system configured to detect radiation scattered from the target in a zero order diffraction direction, and wherein the second detection system comprises a second dispersive element which may be a grating or a prism for dispersion of the radiation scattered from the target in the zero order diffraction direction and a second radiation sensitive device constructed and arranged to measure the intensity of the radiation dispersed from the second dispersive element.

The invention also relates to an inspection apparatus for inspecting a target on a substrate, including a substrate holder for holding the substrate, an illumination system configured to provide an illumination beam for irradiating the target on the substrate, a first detection system configured to detect radiation diffracted from the target in a non-zero order diffraction direction; and wherein the detection system includes a first dispersive element (e.g., a prism or a grating) for dispersion of the radiation diffracted from the target in the non-zero order diffraction direction and a first radiation sensitive device constructed and arranged to measure the intensity of the radiation dispersed by the first dispersive element.

The invention also relates to a method of inspecting a target (e.g., a grating), including providing a substrate with a target on a substrate holder, irradiating the target with an illumination beam, configuring a dispersive element for dispersion of the radiation diffracted from the target in the non zero order direction in the diffracted radiation, and detecting the intensity of the dispersed radiation on a first radiation sensitive device.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
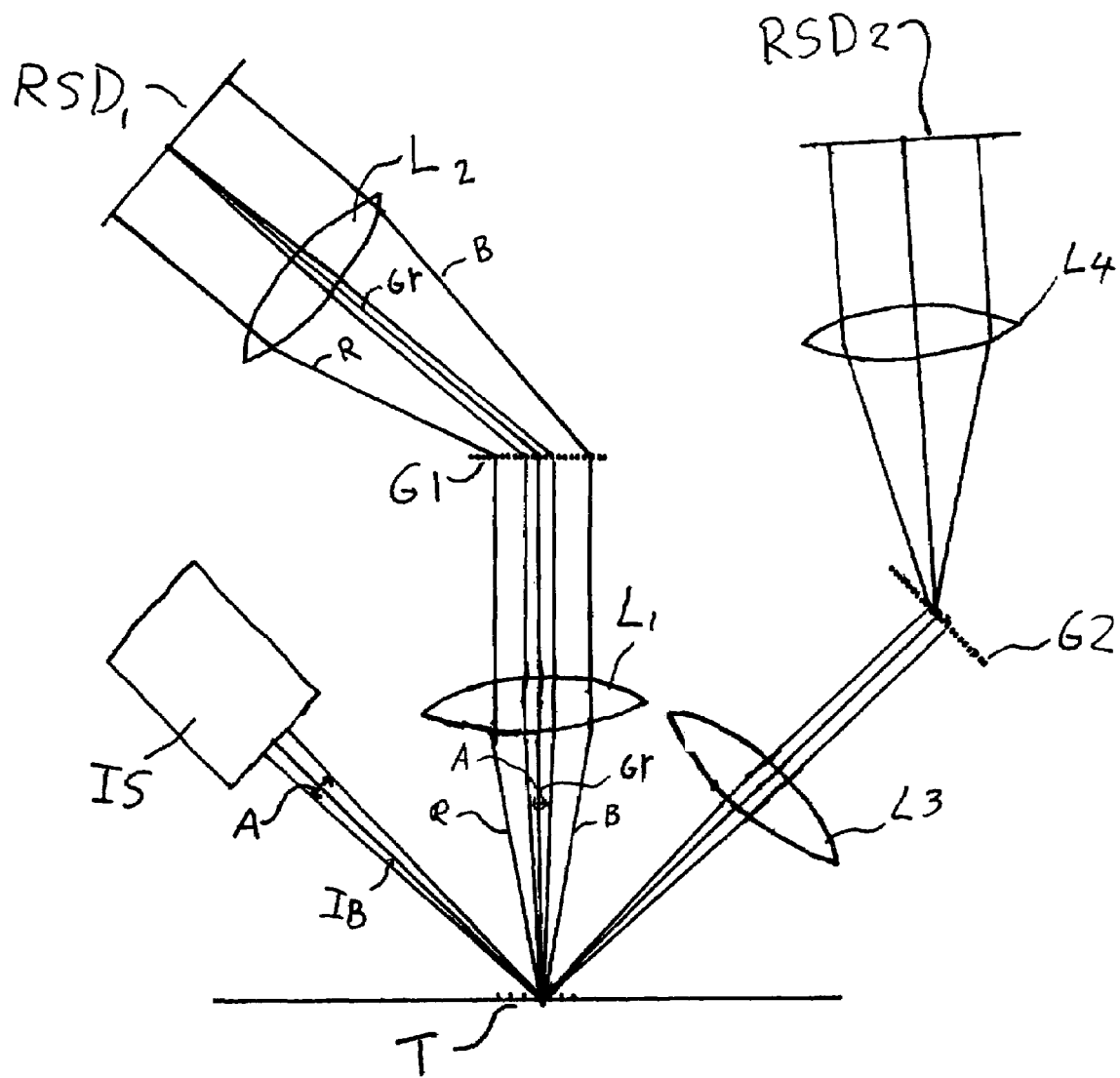
FIG. 1 depicts an inspection apparatus according to an embodiment of the invention.

FIG. 1 schematically depicts an inspection apparatus according to a first embodiment of the invention. The inspection apparatus comprises an illumination system IS for providing an illumination beam IB for irradiating a target T. The illumination system IS may be provided with its own source but also may receive radiation from a separate source. The source may be a broadband source radiating radiation in the 300 to 700 nm range such as for example a Xenon lamp. The target T as shown in FIG. 1 is a grating structure however also other structures may be used as target. The illumination beam is focused on the target with an angle A to have a small illumination spot that is diffracted by the target T in a non-zero order direction and reflected in the zero order direction.

The diffraction causes the illumination beam IB to be separated in sub-beams with different colors, such as for example, red R, green Gr and blue B. The sub-beams red R and blue B are shown as distinct very small beams however in reality are divergent beams having an angle of divergence for every separate wavelength which is equal to the convergence angle A of the illumination beam IB. Only for the green beam Gr the realistic divergence angle A is shown in FIG. 1.

The diffracted radiation in the non-zero order direction is collected by a first lens L1 on a first dispersive element, first grating G1, which alternatively may be a prism. The first grating G1 may have a smaller grating period than a grating period in the structure of the target T. The first grating G1 diffracts the radiation again and the radiation is directed to a first radiation sensitive detector RSD1 by a second lens L2. The combination of the first and second lens L1, L2 focuses the target on a radiation sensitive detector RSD 1. The sub-beams, red R, green Gr and blue B will be focused on the radiation sensitive detector RSD1 dependent on their wavelength and therefore the first radiation sensitive detector RSD1 can measure the intensity of the radiation in the non-zero order direction as a function of the wavelength. The first radiation sensitive device RSD1 is divided in a first direction optically parallel to the direction of the grating period of the first grating in parts. Each part being constructed and arranged to measure the intensity of the radiation on that part.

The scattered radiation in the zero order direction is focused by a lens L3 on a second grating G2. The second grating G2 diffracts the radiation dependent on its wavelength in multiple sub beams which will be directed to the second radiation sensitive detector RSD2 by lens L4. The second radiation sensitive sensor RSD2 can measure the intensity of the radiation in the zero order direction as a function of the wavelength.

While specific embodiments of the invention have been described above, it will be appreciated that the invention may be practiced otherwise than as described. For example, the gratings may be replaced by prisms or other optical means for dispersing radiation with a different wavelength. The description above is intended to be illustrative, not limiting. Thus, it will be apparent to one skilled in the art that modifications may be made to the invention as described without departing from the scope of the claims set out below.

The invention claimed is:

1. An inspection apparatus, comprising:
   an illumination system configured to provide an illumination beam for irradiating a target; and
   a first detection system configured to detect radiation diffracted from the target in a non-zero order diffraction direction, configured to measure the intensity of the radiation diffracted from the target as a function of the wavelength and comprising:
   a first dispersive element to disperse the radiation diffracted from the target in the non-zero order diffraction direction, wherein the first dispersive element is a lateral dispersive element configured to disperse the radiation in a lateral first direction, and
   a first radiation sensitive device constructed and arranged to measure the intensity of the radiation dispersed by the first dispersive element.

2. The apparatus according to claim 1, wherein the illumination beam has a broad bandwidth.

3. The apparatus according to claim 2, wherein the bandwidth is between about 300 nm and about 700 nm.

4. The apparatus according to claim 1 wherein the radiation sensitive device is divided in said first direction in parts, each part constructed and arranged to measure the intensity of the radiation received on that part.

5. The apparatus according to claim 2, wherein the radiation sensitive device is divided in said first direction in parts, each part constructed and arranged to measure the intensity of the radiation received on that part.

6. The apparatus according to claim 1, wherein the first dispersive element is a prism configured and arranged to disperse the radiation in said first direction.

7. The apparatus according to claim 1 wherein the first dispersive element is a grating configured and arranged to disperse the radiation in said first direction.

8. The apparatus according to claim 4, wherein the first dispersive element is a prism configured and arranged to disperse the radiation in said first direction.

9. The apparatus according to claim 4 wherein the first dispersive element is a grating configured and arranged to disperse the radiation in said first direction.

10. The apparatus according to claim 1, wherein the first detection system comprises a lens to project the target upon the first radiation sensitive device.

11. The apparatus according to claim 1, wherein the radiation sensitive device is a CCD array.

12. The apparatus according to claim 1 wherein the illumination beam is irradiated from a xenon source.

13. The apparatus according to claim 1, wherein the inspection apparatus comprises a second detection system configured to detect radiation scattered from the target in a zero order diffraction direction, and comprising:
   a second dispersive element to disperse the radiation scattered from the target in the zero order diffraction direction, and
   a second radiation sensitive device constructed and arranged to measure the intensity of the radiation dispersed from the second dispersive element.

14. The apparatus according to claim 13 wherein the second dispersive element is a grating.

15. An inspection apparatus for inspecting a target on a substrate, comprising:
   a substrate holder configured to hold the substrate;
   an illumination system configured to provide an illumination beam for irradiating the target on the substrate;

a first detection system configured to detect radiation diffracted from the target in a non-zero order diffraction direction, and comprising:
a first dispersive element to disperse the radiation diffracted from the target in the non-zero order diffraction direction in a lateral first direction, and
a first radiation sensitive device constructed and arranged to measure the intensity of the radiation dispersed by the first dispersive element, and divided in the lateral first direction in parts, each part constructed and arranged to measure the intensity of the radiation received on that part.

16. A method of inspecting a target on a substrate, comprising:
irradiating the target with an illumination beam, wherein the target is a grating;
dispersing at least a portion of the radiation diffracted from the target in the non-zero order direction, wherein the dispersing is performed by a grating having a grating period smaller than the period of the target; and
detecting the intensity of the dispersed radiation on a first radiation sensitive device as a function of the wavelength.

17. A method according to claim 16 wherein the illumination beam has a wavelength between about 300 and about 700 nm.

18. An inspection apparatus configured to detect radiation diffracted from a target in a zero order and a non-zero order diffraction direction, the inspection apparatus including:
a first dispersive optical element configured to disperse the radiation diffracted from the target in the non-zero order diffraction direction, wherein the first dispersive optical element is a lateral dispersive element configured to disperse the radiation in a lateral first direction;
a second dispersive optical element configured to disperse the radiation diffracted from the target in the zero order diffraction direction; and
a radiation detector configured to measure an intensity of the radiation dispersed by the first and second dispersive optical elements.

19. The apparatus according to claim 15, wherein the inspection apparatus comprises a second detection system configured to detect radiation scattered from the target in a zero order diffraction direction, and comprising:
a second dispersive element to disperse the radiation scattered from the target in the zero order diffraction direction; and
a second radiation sensitive device constructed and arranged to measure the intensity of the radiation dispersed from the second dispersive element.

* * * * *